(12) United States Patent
Tsutsui (10) Patent No.: US 7,722,566 B2
(45) Date of Patent: May 25, 2010

(54) DEVICE TO DELIVER A POWDERY MEDICINE INTO NASAL CAVITY

(75) Inventor: Tatsuo Tsutsui, Kanagawa (JP)

(73) Assignee: Shin Nippon Biomedical Laboratories, Ltd., Kagoshima (JP)

( * ) Notice: Subject to any disclaimer, the term of this patent is extended or adjusted under 35 U.S.C. 154(b) by 483 days.

(21) Appl. No.: 10/574,220

(22) PCT Filed: Oct. 9, 2003

(86) PCT No.: PCT/JP03/12958

§ 371 (c)(1),
(2), (4) Date: Jul. 7, 2006

(87) PCT Pub. No.: WO2005/035034

PCT Pub. Date: Apr. 21, 2005

(65) Prior Publication Data
US 2007/0060868 A1    Mar. 15, 2007

(51) Int. Cl.
    *A61M 37/00*    (2006.01)
(52) U.S. Cl. .......................... 604/148; 604/58; 604/87; 604/200; 128/203.21
(58) Field of Classification Search .................. 604/58, 604/68, 72, 94.01, 232, 275, 64, 148, 200, 604/87, 244; 128/200.14, 203.15, 203.21, 128/203.22
See application file for complete search history.

(56) References Cited

U.S. PATENT DOCUMENTS

| 4,013,075 | A | * | 3/1977 | Cocozza | 128/203.15 |
| 4,105,027 | A | * | 8/1978 | Lundquist | 128/203.15 |
| 5,250,287 | A | * | 10/1993 | Cocozza | 424/45 |
| 5,651,359 | A | * | 7/1997 | Bougamont et al. | 128/203.15 |
| 5,810,004 | A | * | 9/1998 | Ohki et al. | 128/203.15 |
| 5,899,202 | A | * | 5/1999 | Ohki et al. | 128/203.22 |
| 5,921,236 | A | * | 7/1999 | Ohki et al. | 128/203.15 |
| 5,989,217 | A | * | 11/1999 | Ohki et al. | 604/94.01 |
| 6,298,846 | B1 | * | 10/2001 | Ohki et al. | 128/203.15 |

(Continued)

FOREIGN PATENT DOCUMENTS

GB    1338254    11/1973

(Continued)

OTHER PUBLICATIONS

English language Abstract of JP 2003-154006.

(Continued)

*Primary Examiner*—Kevin C Sirmons
*Assistant Examiner*—Kami A Bosworth
(74) *Attorney, Agent, or Firm*—Greenblum & Bernstein, P.L.C.

(57) ABSTRACT

A device that delivers a powdery medicine for a nasal cavity includes positioning guides that cause a capsule to slide as far as a predetermined position and are provided on the side of cutters to make holes on both ends of the capsule provided between the connection port on the side of a nozzle that sprays the powdery medicine into the nasal cavity. The device further includes a connection port on the side of a pump that supplies spray air to the nozzle in order to make the size of the holes made on both ends of the capsule constant, wherein a distance between the connection ports is made shorter than a distance between blade tips of the cutters.

6 Claims, 5 Drawing Sheets

U.S. PATENT DOCUMENTS

| | | | |
|---|---|---|---|
| 6,341,605 B1 * | 1/2002 | Ohki et al. | 128/203.15 |
| 6,408,846 B1 * | 6/2002 | Ohki et al. | 128/203.15 |
| 6,772,755 B2 * | 8/2004 | Pera | 128/203.15 |
| 2001/0020472 A1 * | 9/2001 | Horlin | 128/203.15 |
| 2002/0033177 A1 * | 3/2002 | Ohki et al. | 128/203.15 |
| 2002/0092521 A1 * | 7/2002 | Sullivan et al. | 128/200.24 |
| 2002/0158150 A1 * | 10/2002 | Matsugi et al. | 239/418 |
| 2002/0162552 A1 * | 11/2002 | Pera | 128/203.15 |
| 2003/0015195 A1 * | 1/2003 | Haaije de Boer et al. | 128/203.15 |
| 2005/0177095 A1 | 8/2005 | Tsutsui | 604/58 |

FOREIGN PATENT DOCUMENTS

| | | |
|---|---|---|
| JP | 46-4094 | 11/1971 |
| JP | 46-49094 | 11/1971 |
| JP | 9-276405 | 10/1997 |
| JP | 2003-154006 | 5/2003 |

OTHER PUBLICATIONS

English language Abstract of JP 9-276405.
U.S. Appl. No. 10/550,490, filed Sep. 26, 2005, Tsutsui.

* cited by examiner

DEVICE TO DELIVER A POWDERY MEDICINE INTO NASAL CAVITY

This application is a national stage application filed under 35 U.S.C. 371 based on International Application No. PCT/JP03/01958 filed Oct. 9, 2003.

TECHNICAL FIELD

The present invention concerns a device to deliver a powdery medicine into nasal cavity that delivers a powdery medicine filled in a capsule into a nasal cavity.

BACKGROUND ART

An existent device to deliver a powdery medicine into a nasal cavity of a patient suffering from asthma or nasal allergy (refer, for example, to JP-A No. 46-4094) is adapted for detaching a cap-type nozzle fitted detachably to the top end of a cylindrical member formed with an air discharge port of a pump that discharges air by squeezing a rubber ball with a hand, attaching a capsule filled with a powdery medicine to the inside of the cylindrical member, fitting the nozzle again to the top end of the cylindrical member, then pressing the pump formed as the rubber ball so as to squeeze in the direction of the nozzle, protruding the pointed top end of a needle contained in the pump passing through the capsule loaded in the cylindrical member from the air discharge port of the pump to a position reaching the nozzle, thereby making holes on both ends of the capsule and supplying air driven out of the air discharge port of the pump flowing through the inside of the capsule to the nozzle and spraying the powdery medicine in the capsule from the nozzle.

However, in the device described above, the operation is extremely troublesome since this requires to detach or attach the cap-type nozzle from or to the top end of the cylindrical member upon loading the capsule in the cylindrical body or take-out a used capsule from the inside of the cylindrical member, or press the pump so as to squeeze in the direction of the nozzle to protrude the needle contained in the pump after loading the capsule in the cylindrical member in order to make the holes on both ends of the capsule.

Further, after pressing the pump so as to be squeezed in the direction of the nozzle to make the holes on both ends of the capsule loaded in the cylindrical member by the needle protruded from the inside of the pump, when the pressed state of the pump is released for retracting the protruded needle into the pump, the powdery medicine in the capsule is sucked from the holes made to the end of the capsule on the side of the pump by the suction force generated upon recovery of the pump into an original shape and may possibly be sucked from the air discharge port of the pump into the inside of the pump.

Further, upon making the holes on both ends of the capsule, holes are not sometimes made at the ends of the capsule on the side of the nozzle depending on the case since the pump is not pressed to a position where the pointed top of the needle contained in the pump penetrates the capsule and, when the pump is actuated in this state, it may possibly cause a worry not only that the powdery medicine in the capsule is not sprayed from the nozzle, but also a portion of the powdery medicine may possibly be sucked into the pump.

Further, upon sticking the needle for making holes from one to the other side of the capsule loaded in the cylindrical member so as to be sandwiched between the air discharge port of the pump and the nozzle to make holes, since the end of the capsule is concaved inward by the pressing force of the needle to form a gap between the hole made at the end and the air discharge port of the pump or between the hole and the nozzle, the powdery medicine in the capsule can not be sprayed efficiently from the nozzle but a portion of the powdery medicine scatters into the cylindrical member to possibly cause a worry that the powdery medicine can not be sprayed by a necessary amount into the nasal cavity.

Further, when the needle is stuck to make holes on both ends of the capsule, since residues of the capsule broken through by the needle protrude at the periphery of the hole to hinder the flow of air for supplying the powdery medicine in the capsule to the nozzle, it may possibly cause a disadvantage that the entire amount of the powdery medicine in the capsule can not be discharged but remains in the capsule.

Then, the present applicant has developed a device capable of simply loading a capsule by one-touch operation and, at the same time, making holes on both ends of the capsule upon loading automatically, as well as with no worry of concaving the both ends of the capsule inward or scattering the powdery medicine in the capsule upon making the holes and also with no worry that residues of the capsule protrude to the periphery of the hole which may possibly hinder the air flow (refer, for example, to JP-A No. 2003-154006).

In the device, a capsule having holes formed on both ends in communication with a connection port on the side of the nozzle for spraying a powdery medicine into a nasal cavity and a connection port on the side of a pump for supplying atomized air to the nozzle is loaded between both of the connection ports and sprayed air is supplied from the pump through the inside of the capsule to the nozzle, thereby spraying the powdery medicine filled in the capsule, in which a capsule holder for loading the capsule between the connection port on the side of the nozzle and the connection port on the side of the pump is placed moveably forward and backward relative to a capsule mounting position, and both ends of the capsules held to the capsule holder and moving forward to a loading position between the connection port on the side of the pump and the connection port on the side of the nozzle are automatically cut off partially by a cutter thereby making holes on both ends thereof. Accordingly, it is possible to rapidly conduct the loading operation of capsule, the hole making operation of capsule, and the ejecting operation of the spent capsule in one-touch procedure.

Further, when both ends of the capsule are cut off by a cutter to make the holes, since residues that hinder the air flow are not formed at the periphery of the holes, the powdery medicine in the capsule can be sprayed thoroughly. Further, since both ends of the capsule are not concaved inward, there is less worry that gaps are formed between both ends thereof, and the connection port on the side of the nozzle and the connection port on the side of the pump to scatter the powdery medicine in the capsule through the gaps.

However, in a test for practical use of the device described above, it has been found that the diameter of the holes opened on both ends of the capsule varies and, in a case where the hole diameter is smaller than the open diameter of the connection port on the side of the nozzle or the connection port on the side of the pump, it is difficult to thoroughly discharge the powdery medicine in the capsule by the operation of the pump only for once. Further, in a case where the diameter of the holes made on both ends of the capsule is made substantially identical with or larger than the open diameter of the connection port on the side of the nozzle and the connection port on the side of the pump, while the powdery medicine in the capsule can be discharged most effectively, it has been found, in this case, that when a great amount of spray air is supplied instantaneously into the capsule by strongly gripping and squeezing the entire pump, the spray air leaks partially from the both ends of the capsule that abuts against the connection port on the side of the nozzle and the connection port on the side of the pump to scatter the powdery medicine in the capsule.

DISCLOSURE OF THE INVENTION

The technical subject of the present invention is to prevent variation in the diameter of holes made on both ends of a capsule thereby enabling to make holes each having a predetermined diameter at a high accuracy, as well as prevent spray air supplied by a pump from leaking through the both ends of the capsule that abuts against both connection ports to scatter a powdery medicine in the capsule even in a case where the diameter of the holes made on both ends of the capsule is made substantially identical with or greater than the open diameter of the connection port on the side of the nozzle and the connection port on the side of the pump in order to efficiently spray the powdery medicine in the capsule.

For solving the subject described above, the invention according to claim 1 provides a device to deliver and dose a powdery medicine for a nasal cavity for spraying the powdery medicine filled in a capsule by loading a capsule between a connection port on the side of the nozzle for spraying the powdery medicine into the nasal cavity and a connection port on the side of a pump for supplying spray air to the nozzle, the capsule being formed with holes on both ends in communication with both of the connection ports and supplying spray air from the pump through the capsule to the nozzle, characterized in that a capsule holder for holding the capsule filled with the powdery medicine slidably in the longitudinal direction thereof and loading the same between the connection port on the side of the nozzle and the connection port on the side of the pump is placed moveably forward and backward relative to a loading position of the capsule, a cutter for partially cutting off both ends of the capsule that moves forward to the loading position while being held by the capsule holder to make holes on both ends thereof is placed, and a positioning guide is located on this side of the cutter for guiding both ends of the capsule that moves forward to the loading position while being held by the capsule holder and causing the capsule to slide as far as a predetermined position.

Further the invention according to claim 4 provides a device to deliver and dose a powdery medicine into a nasal cavity for spraying a powdery medicine filled in a capsule by loading a capsule between a connection port on the side of the nozzle for spraying the powdery medicine into the nasal cavity and a connection port on the side of a pump for supplying spray air to the nozzle, the capsule being formed with holes on both ends in communication with both of the connection ports and supplying spray air from the pump through the capsule to the nozzle, characterized in that a capsule holder for loading the capsule filled with the powdery medicine between the connection port on the side of the nozzle and the connection port on the side of the pump is placed moveably forward and backward relative to a loading position of the capsule, a cutter for partially cutting off both ends of the capsule that moves forward to the loading position while being held by the capsule holder to make holes on both ends thereof is placed, and a distance between the connection port on the since of the nozzle and the connection port on the side of the pump is made shorter than the length of the capsule the both ends of which are cut off by the cutter, so that both ends of the capsule loaded between them are pressed by peripheral portions of both of the connection ports.

In the device to deliver and dose a powdery medicine into the nasal cavity according to claim 1 of the present invention, in the course of slidably holding the capsule filled with the powdery medicine by the capsule holder in the longitudinal direction and moving the same forward to the loading position between the connection port on the side of the nozzle and the connection port on the side of the pump, the capsule is caused to slide to a predetermined position being guided at the both ends by the positioning guide, and both ends of the capsule are always cut off at the predetermined position to form holes on both ends. Accordingly, the diameter of the holes opened on both ends of the capsule does not vary and holes each of an appropriate size capable of most effectively discharging the powdery medicine in the capsule can be opened at a high accuracy.

In the device to deliver and dose a powdery medicine into a nasal cavity according to the claim 4 of the invention, since both ends of the capsule loaded between the connection port on the side of the nozzle and the connection port on the side of the pump are strongly contacted to the peripheral portions of both connection ports by repulsion generated upon pressing of both of the connection ports by the peripheral portions, there is no worry that spray air supplied by the pump leaks from both ends of the capsule to scatter the powdery medicines in the capsule even in a case where the diameter of the holes made on both ends of the capsule is made substantially identical or larger than the open diameter for the connection port on the side of the nozzle and the connection port on the side of the pump.

BEST MODE FOR PRACTICING THE INVENTION

In a best mode of the device to deliver a powdery medicine into a nasal cavity according to the present invention, a capsule holder for holding a capsule filled with a powdery medicine slidably in the longitudinal direction thereof and loading the capsule between a connection port on the side of a nozzle of spraying the powdery medicine into the nasal cavity and a connection port on the side of a pump for supplying spray air to the nozzle is placed moveably forward and backward to a loading position of the capsule, a cutter for partially cutting off both ends of the capsule that moves forward to the loading position while being held by a capsule holder to make holes on both ends is placed, a positioning guide is located on this side of the cutter for guiding both ends of the capsule that moves forward to the loading position while being held by the capsule holder and causing the capsule to slide as far as a predetermined position, and the distance between the connection port on the side of the nozzle and the connection port on the side of the pump is made shorter than the length of the capsule after cutting off both ends thereof by the cutter, so that both ends of the capsule loaded therebetween are pressed by peripheral portions of both of the connection ports.

A best mode for practicing the invention is to be described with reference to the accompanying drawings.

In a device to deliver a powdery medicine into a nasal cavity according to this embodiment, a forked nozzle 1 for spraying a powdery medicine into right and left nasal cavities simultaneously and a pump 2 for supplying a spray air to the nozzle 1 are attached to a main body 3, in which a connection port 7 on the side of the nozzle and a connection port 8 on the side of the pump that connect the nozzle 1 and the pump 2 by way of a capsule having holes 5, 6 opened on both ends are formed, and a capsule holder 10 for loading the capsule 4 filled with the powdery medicine 9 between the connection port 7 on the side of the nozzle and the connection port 8 on the side of the pump while slidably holding the same in the longitudinal direction thereof is located moveably forward and backward relative to the loading position.

Further, cutters 11a, 11b for partially cutting off both ends of the capsule 4 that is moved forward while being held by the capsule holder 10 to the capsule loading position between the connection port 7 on the side of the nozzle and the connection port 8 on the side of the pump thereby making holes 5, 6 in communication with the connection ports 7, 8 on both ends thereof are provided to the body 3, and positioning guides 12a, 12b are located for guiding both ends of the capsule 4 that is moved forward while being held by the capsule holder 10 to the loading position and causing the capsule 4 to slide as far as a predetermined position are provided on this side of the cutters 11a, 11b.

The cutters 11a, 11b include a pair of blades secured in parallel with each other with the blade tips being directed to the direction opposing the advancing direction of the capsule holder 10, and the positioning guides 12a and 12b are formed of a pair of protrusions opposed to each other. Further, storage spaces 13a, 13b are formed between the blades forming the cutters 11a, 11b and the protrusions forming the positioning guides 12a, 12b located on this side thereof for discharging cut ends of the capsule cut off by the cutters 11a, 11b.

The distance between the positioning guides 12a and 12b is set to a distance corresponding to the shortest length for the capsule length causing dimensional variation during manufacture of capsules. Further, the cutters 11a, 11b are situated at the position that the tops of the spherical surface forming both ends of the capsule 4 positioned by the positioning guides 12a, 12b to the predetermined position are cut off each by a predetermined area so that holes 5, 6 each having a diameter substantially equal with or somewhat larger than the open diameter of the connection ports 7, 8 can be opened on both ends of the capsule 4. That is, the diameter for the holes 5, 6 formed on both ends of the capsule 4 by the cutters 11a, 11b is set to the size substantially identical with or larger than the open diameter of the connection ports 7, 8 in communication with the holes 5, 6.

Further, the distance L between the connection port 7 on the side of the nozzle and the connection port 8 on the side of the pump, for loading the capsule 4 having holes 5, 6 each of a predetermined diameter opened by cutting off both ends thereof by the cutters 11a, 11b is made smaller than the distance M between blade tips of the cutters 11a and 11b for cutting off the both ends of the capsule 4. That is, the distance L between the connection ports 7 and 8 is made shorter than the length of the capsule 4 after cutting off both ends thereof by the cutters 11a, 11b, so that both ends of the capsule 4 loaded between the connection ports 7 and 8 are pressed by the peripheral portions 14 and 15 of both of the connection ports 7 and 8.

The nozzle 1 is made of a tube 16 which is soft and flexible so as not to damage the inside of the nasal cavity. Further, in the pump 2, an open end of the pump main body 17 molded from a rubber or plastic material having a rubbery elasticity into a hollow body which can be deformed under compression is secured in an air tight manner to one end of the body 3 formed with the connection port 8 on the side of the pump, and an air suction port 18 having a valve body 19 as a check valve for checking the flow of air from the inside of the pump body 17 is located at a position opposite to the open end of the pump main body 17.

Further, an air discharge port 20 of the pump 2 in communication from the inside of the pump main body 17 to the connection port 8 is formed on one end of the body 3 to which the open end of the pump main body 17 is fixed, and a check valve 21 is located in the air discharge port 20 for inhibiting the inflow of air from the side of the connection port 8 to the inside of the pump main body 17 when the pump main body 17 deformed under compression recovers its original shape. The check valve 21 is adapted such that a valve body 22 for opening/closing the air discharge port 20 is resiliently biased in the direction of closing the valve by a spring 23 and the valve body 22 is driven to the valve opening direction against the resilient force of the spring 23 by an air pressure in the pump main body 17 exerting on the end face of the valve body 22 that closes the air discharge port 20 when the pump main body 17 is gripped and squeezed by a hand.

The capsule holder 10 has a drawer type main body 25 inserted into and drawn out of a space 24 in the body 3 formed between the connection ports 7 and 8, in which a recessed groove 26 is formed on the surface thereof for slidably holding the capsule 4 filled with a powdery medicine 9 in the longitudinal direction so as to protrude both ends thereof, and a stopper 28 is formed on the back of the main body 25 for engagement with a protrusion 27 formed on the inlet to the space 24 of the body 3 such that the body 3 is not detached from the body 3, and a recessed groove 29 in engagement with the protrusion 27 is formed for slidably supporting the main body 25 in the direction of inserting and drawing the same into and out of the space 24 of the body 3.

Figure 1:
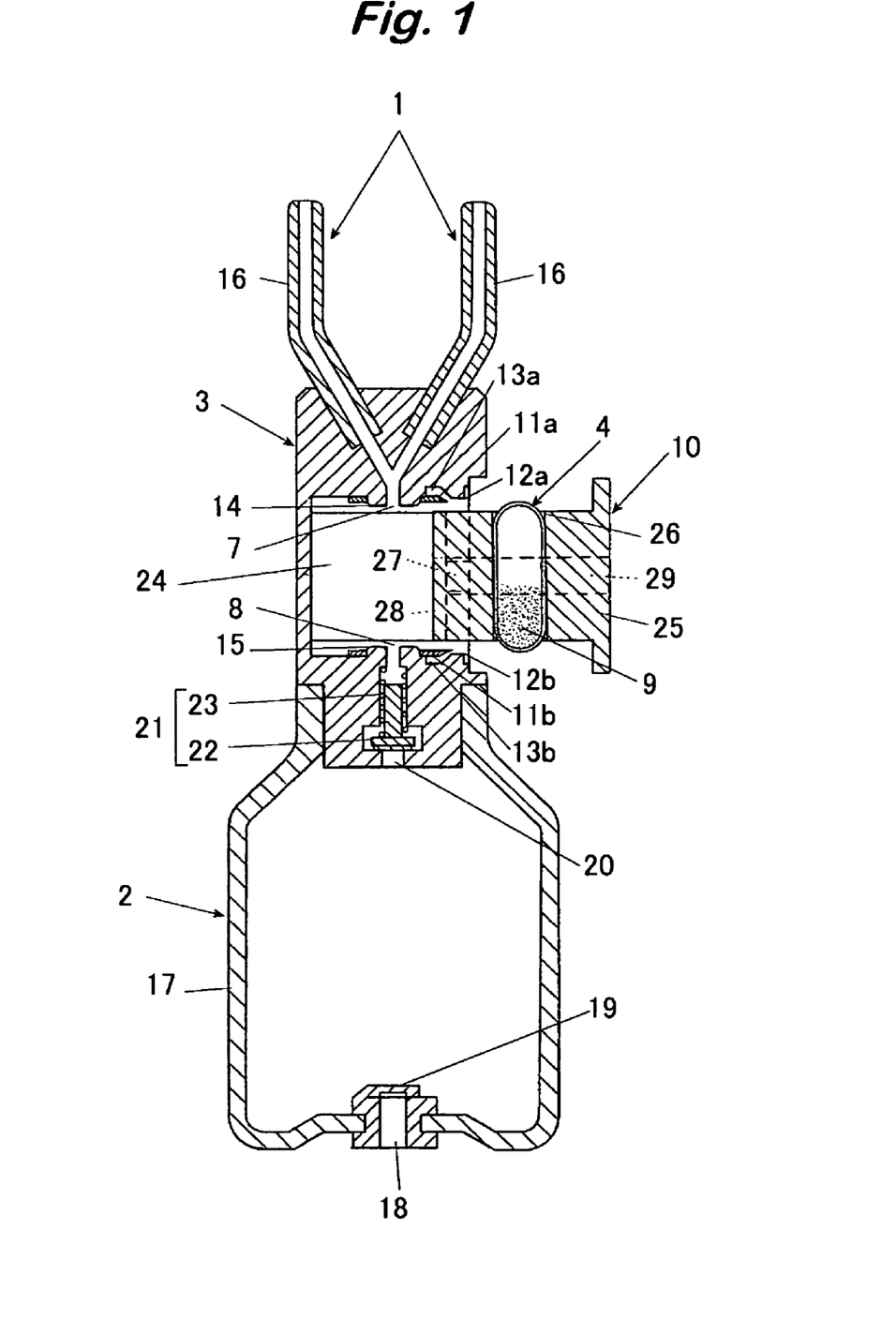
FIG. 1 is a cross sectional view showing an example of a device according to the present invention.
Figure 2:
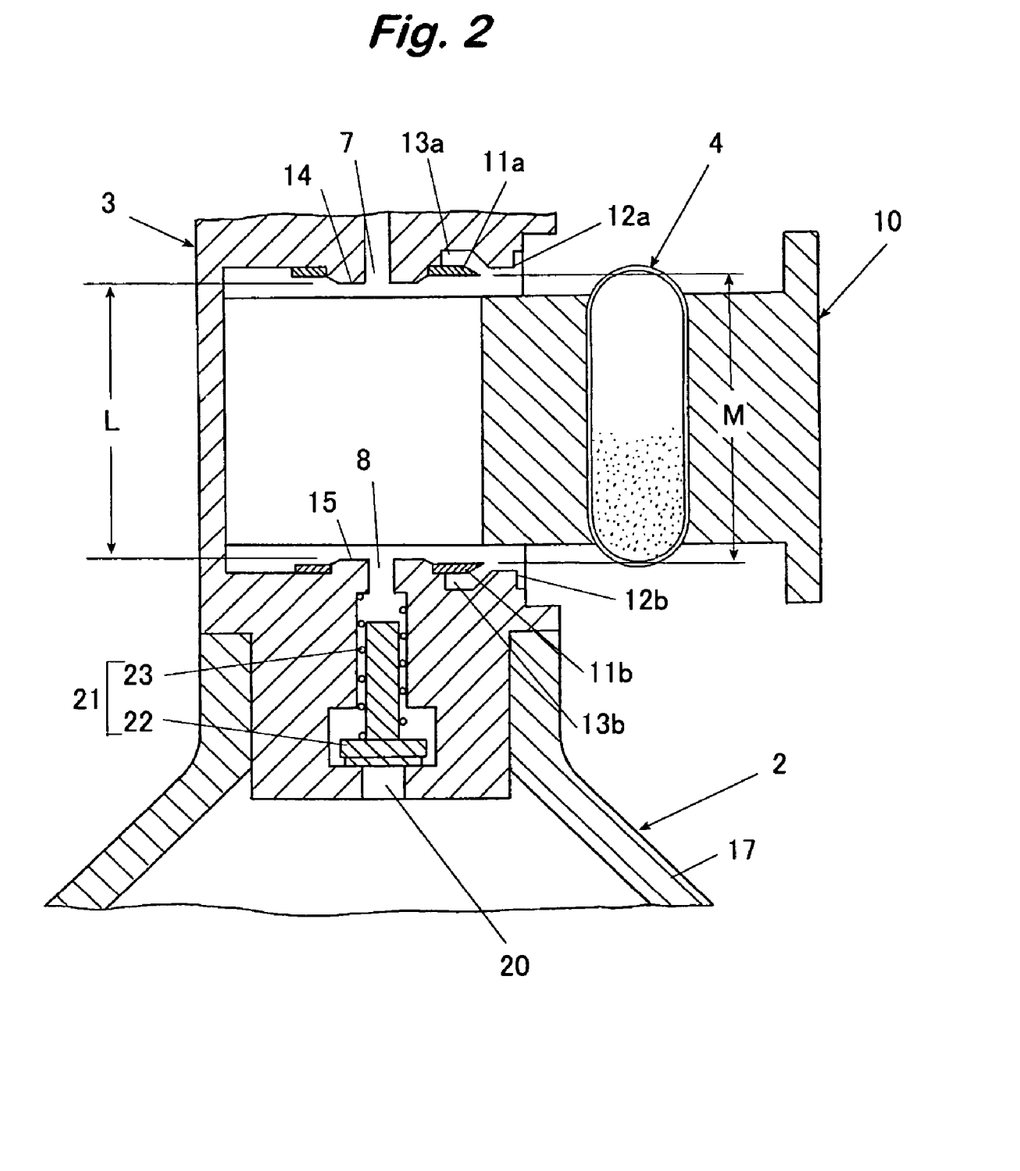
FIG. 2 is an enlarged fragmentary view of FIG. 1.
Figure 3:
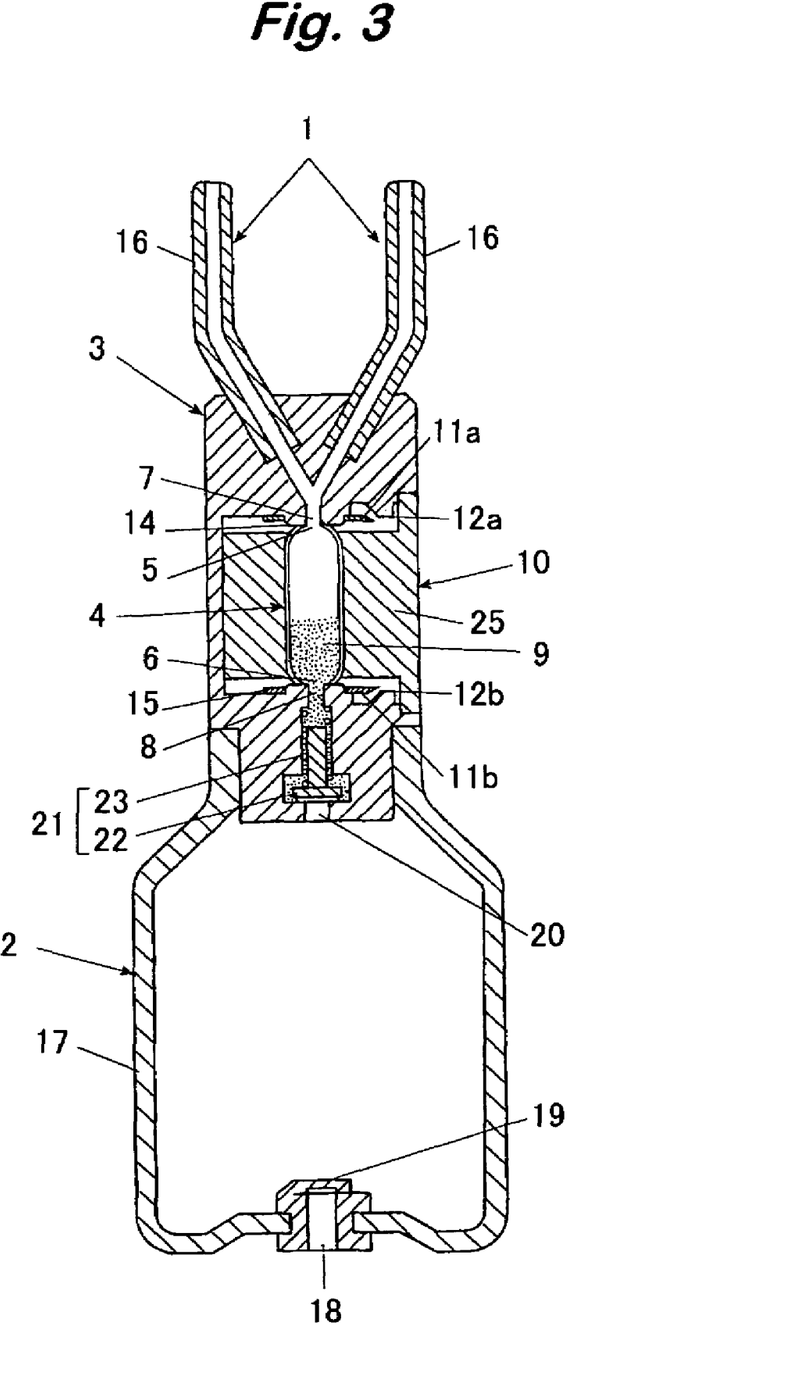
FIG. 3 is a cross section view of the device according to the present invention showing the state of loading a capsule.

The device of the embodiment is constituted as has been described above, and the method of using and the operation thereof are to be explained. At first, the main body 25 of the capsule holder 10 is drawn out of the space 24 of the body 3 and the capsule 4 is held in the recessed groove 26 formed on the surface of the main body 25 as shown in FIG. 1, and then the main body 25 is inserted into the space 24 of the body 3 as shown in FIG. 3.

Then, the capsule 4 held in the capsule holder 10 is caused to slide as far as the predetermined position being guided at both ends by the positioning guides 12a, 12b, the both ends are partially cut off at the predetermined position by the cutters 11a, 11b, by which holes 5 and 6 each having a diameter substantially identical with or somewhat larger than the open diameter of the connection ports 7 and 8 on both ends are opened at a good accuracy, then the capsule is loaded between the connection ports 7 and 8. Then, the capsule 4 loaded between the connection ports 7 and 8 are in communication at the holes 5 and 6 opened on both ends with the connection ports 7 and 8 and, at the same time, both ends thereof are pressed by peripheral portions 14 and 15 of the connection ports 7 and 8 and strongly brought into intimate contact with the peripheral portions 14 and 15.

Figure 4:
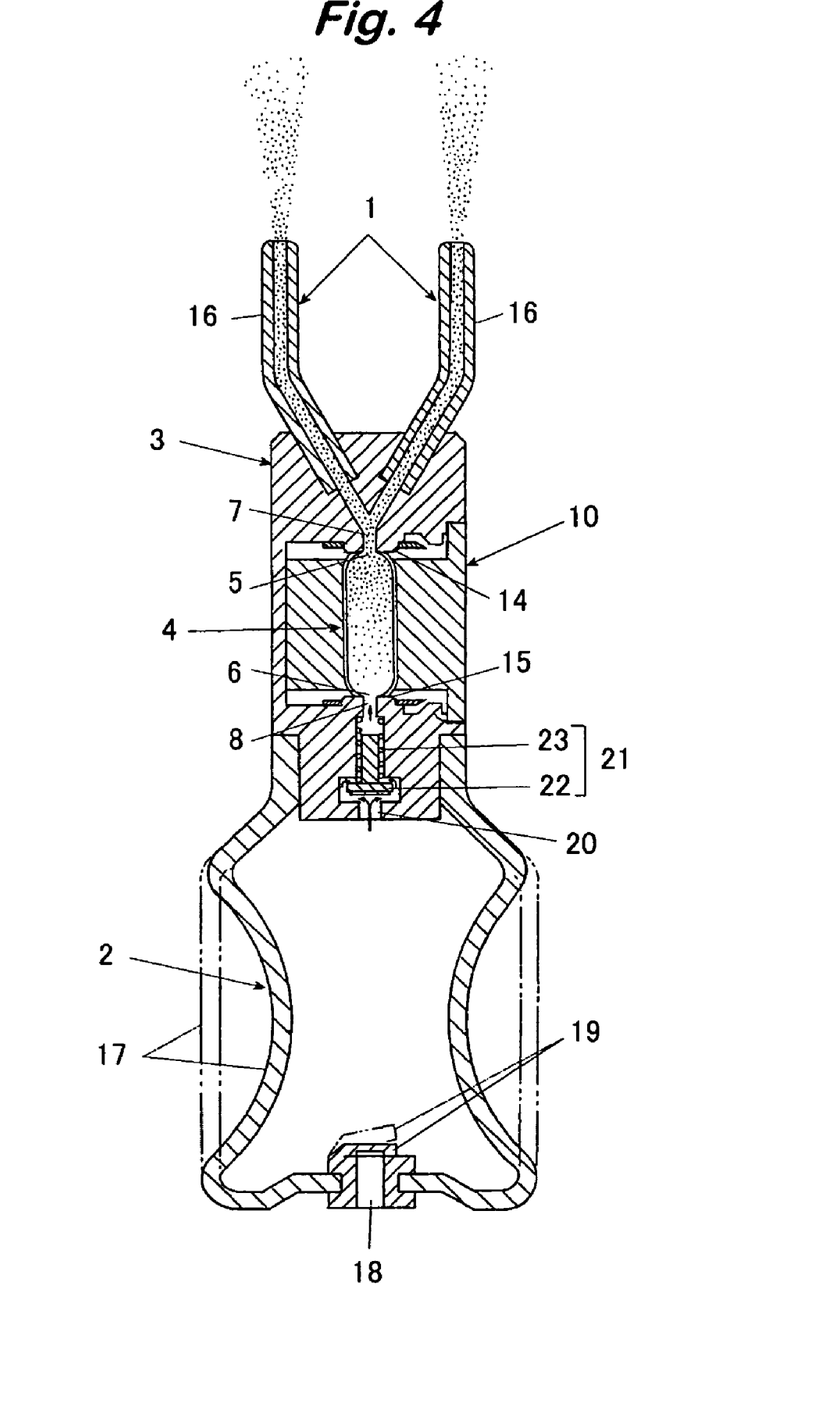
FIG. 4 is a cross sectional view of the device according to the present invention showing a state where a powdery medicine in the capsule is sprayed.

In this state, when the nozzle 1 is inserted into nasal cavities and the pump main body 17 is gripped and squeezed from the state shown by a chained line in FIG. 4 to the state shown by a solid line in the drawing, air pressure in the pump main body 17 increases to open the check valve 21 that closes the air discharge port 20 of the pump 2, spray air driven out from the inside of the pump main body 17 enters from the hole 6 on one end of the capsule 4 in communication with the connection port 8 into the capsule 4, flows through the inside of the capsule 4 and is supplied from the hole 5 on the other end of the capsule 4 by way of the connection port 7 in communication with the hole 5 to the nozzle 1, and the powdery medicine 9 filled in the capsule 4 is sprayed by the spray air from the top end of the nozzle 1 and dosed into the nasal cavities.

In this process, since the spray air supplied by the pump 2 to the nozzle 1 flows smoothly from the connection port 8 on the side of the pump 2 by way of the inside of the capsule 4 to the connection port 7 on the side of the nozzle with no stagnation in a case where the diameter for the holes 5, 6 of the capsule 4 for communication with the connection port 7 on the side of the nozzle and the communication port 8 on the side of the pump has a size substantially equal with or larger than the open diameter of the connection ports 7, 8, the powdery medicine 9 in the capsule 4 can be supplied with no residues by the spray air to the nozzle 1.

Figure 5:
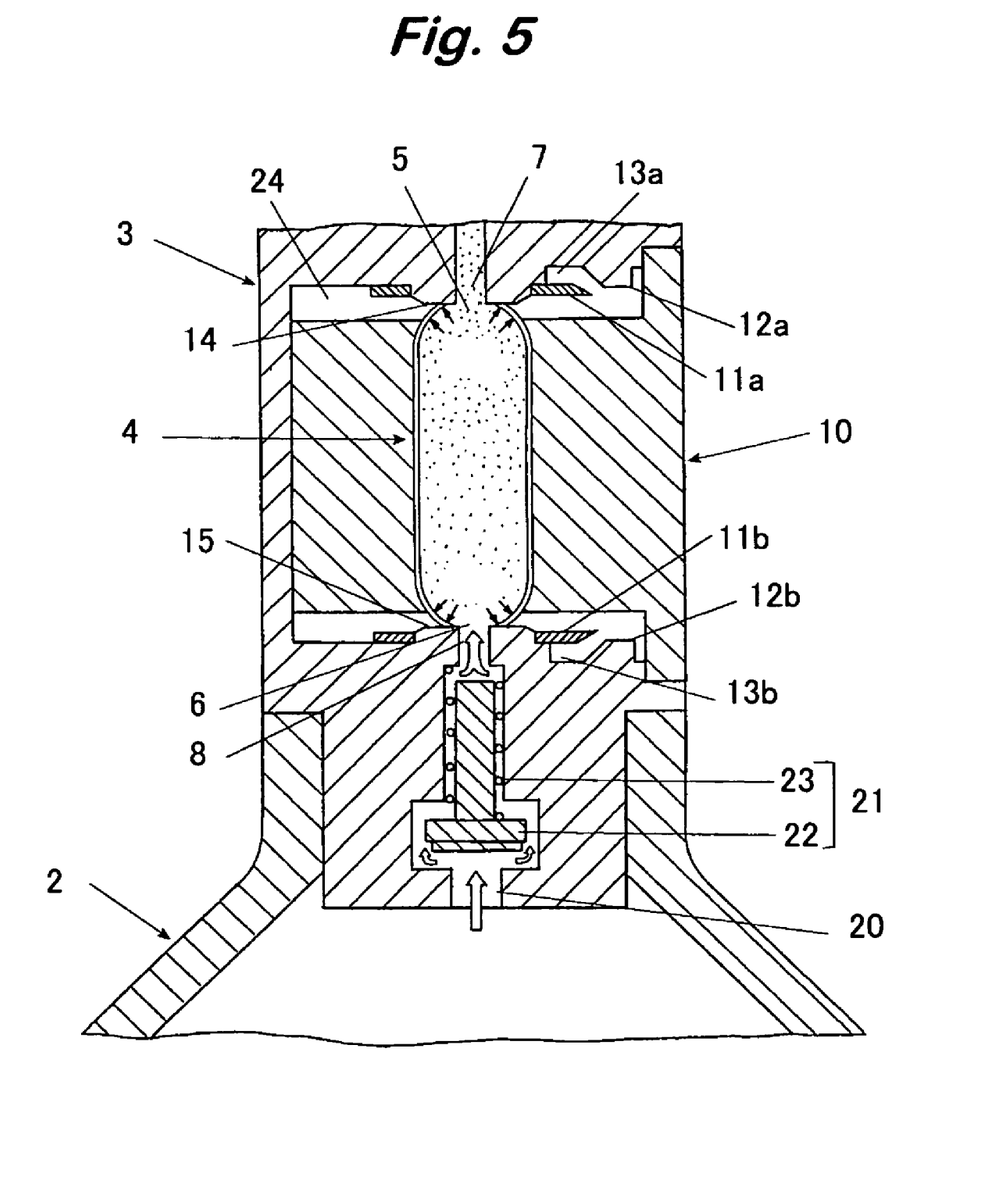
FIG. 5 is an enlarged fragmentary view of FIG. 4.

Further, since the both ends of the capsule 4 loaded between the connection port 7 on the side of the nozzle and the connection port 8 on the side of the pump are pressed by the peripheral portions 14 and 15 of both of the connection ports 7 and 8 and are strongly brought into intimate contact with the peripheral portions 14 and 15, even when a great amount of spray air is supplied instantaneously into the capsule 4, there is no worry that the powdery medicine 9 leaks and scatters from both ends of the capsule 4 in communication with the connection ports 7 and 8. In addition, when a great amount of spray air is supplied instantaneously into the capsule 4, since the inner pressure of the capsule 4 increases to also exert a force of pressing both ends of the capsule 4 from the inside thereof to the peripheral portions 14 and 15 of the connection ports 7 and 8, and the intimate contact between the peripheral portions 14 and 15 and both ends of the capsule 4 is further enhanced to attain an air tight state between them, leaking and scattering of the powdery medicine 9 from both ends of the capsule 4 can be prevented reliably and the powdery medicine can be delivered and dosed in a necessary amount accurately into the nasal cavities. While the nozzle 1 is a forked nozzle in this embodiment, the nozzle used in the invention is not restricted to the forked type but may also be a single tube type nozzle.

INDUSTRIAL APPLICABILITY

As described above, the device to deliver a powdery medicine for the nasal cavity according to the invention is suitable for application use of deliver by spraying a powdery medicine filled in a capsule into nasal cavities reliably and easily.

The invention claimed is:

1. A device to deliver a powdery medicine for nasal cavity to spray a powdery medicine filled in a capsule by loading the capsule between a connection port on a side of a nozzle to spray the powdery medicine into the nasal cavity and a connection port on a side of a pump that supplies spray air to the nozzle, the capsule being formed with a hole on each end in communication with a respective one of the connection ports and supplying spray air from the pump through the inside of the capsule to the nozzle, the device comprising:

a main body having a loading space and configured to hold the capsule between the connection ports;

a capsule holder that holds the capsule filled with the powdery medicine and is slidably movable from the main body, the capsule holder configured to position the capsule in a loading position in the loading space between the connection port on the side of the nozzle and the connection port on the side of the pump, the capsule holder being movable forward and backward relative to the loading position of the capsule;

a cutter that partially cuts off both ends of the capsule as the capsule moves forward to the loading position while being held by the capsule holder such that the cutter makes the holes on opposite ends of the capsule, the cutter including a pair of blades secured in parallel with each other at opposite sides of the loading space in a sliding direction of the capsule holder between the connection ports, each blade having a blade tip directed in a direction opposing the sliding direction of the capsule holder towards the loading position; and a positioning guide located forwardly of the cutter to guide the ends of the capsule that move forward to the loading position while being held by the capsule holder and causing the capsule to slide as far as a predetermined position, wherein peripheral portions of the main body that define at least a portion of both of the connection ports are formed as seal projections that project from surfaces of the blades toward the loading space, and the distance between the seal projections is shorter than the length of the capsule after cutting off both ends by the cutter, so that both ends of the capsule loaded between them are pressed by both seal projections.

2. The device to deliver a powdery medicine for a nasal cavity according to claim 1, wherein the positioning guide includes a pair of protrusions opposed to each other and a storage space is formed between the blades and the protrusions placed on a side thereof for discharging cut ends of the capsule cut off by the blades.

3. The device to deliver a powdery medicine for a nasal cavity according to claim 2, wherein the capsule holder is configured in the manner of a drawer having a recessed groove to hold the capsule, and to move forward and backward relative to the loading position of the capsule.

4. The device to deliver a powdery medicine for a nasal cavity according to claim 1, wherein the capsule holder is configured in the manner of a drawer having a recessed groove to hold the capsule, and to move forward and backward relative to the loading position of the capsule.

5. A device to deliver a powdery medicine for a nasal cavity to spray a powdery medicine filled in a capsule by loading the capsule between a connection port on a side of a nozzle to spray the powdery medicine into the nasal cavity and a connection port on a side of a pump that supplies spray air to the nozzle, the capsule being formed with a hole on each end in communication with a respective one of the connection ports and to receive spray air from the pump through the inside of the capsule to the nozzle, the device comprising:

a main body having a loading space and configured to hold the capsule between the connection ports;

a capsule holder that holds the capsule filled with the powdery medicine, the capsule holder being movable between the connection port on the side of the nozzle and the connection port on the side of the pump, the capsule holder being movable forward and backward relative to a loading position of the capsule in the loading space of the main body; and a cutter that partially cuts off both ends of the capsule as the capsule moves forward to the loading position while being held by the capsule holder such that the cutter makes the holes on opposite ends of the capsule, the cutter includes a pair of blades secured in parallel with each other at opposite sides of the loading space in a sliding direction of the capsule holder between the connection ports, each blade having a blade tip directed in a direction opposing the sliding direction of the capsule holder towards the loading position, wherein peripheral portions of the main body that define at least a portion of both of the connection ports are formed as seal projections that project from surfaces of the blades toward the loading space, and the distance between the seal projections is shorter than the length of the capsule after cutting off both ends by the cutter, so that both ends of the capsule loaded between them are pressed by both seal projections.

6. The device to deliver a powdery medicine for a nasal cavity according to claim 5, wherein the diameter for each hole formed on each end of the capsule by the cutter is set to a size substantially identical with or larger than the diameter for the opening of each of the connection ports in communication with the hole.

\* \* \* \* \*